United States Patent [19]
Yoon

[11] Patent Number: 5,578,053
[45] Date of Patent: *Nov. 26, 1996

[54] SAFETY NEEDLE INSTRUMENT HAVING A TRIGGERED SAFETY MEMBER

[76] Inventor: InBae Yoon, 2101 Highland Ridge Dr., Phoenix, Md. 21131

[ * ] Notice: The term of this patent shall not extend beyond the expiration date of Pat. No. 5,431,635.

[21] Appl. No.: 115,152

[22] Filed: Sep. 2, 1993

Related U.S. Application Data

[63] Continuation-in-part of Ser. No. 83,220, Jun. 24, 1993, Pat. No. 5,431,635, and Ser. No. 83,728, Jun. 29, 1993, Pat. No. 6,466,224.

[51] Int. Cl.$^6$ ..................................................... A61M 5/00
[52] U.S. Cl. ........................... 606/185; 606/165; 606/170
[58] Field of Search ..................................... 128/751, 752, 128/753, 754, 4, 6; 604/95, 158, 162, 163, 164, 165, 170, 272, 274, 280, 169

[56] References Cited

U.S. PATENT DOCUMENTS

| | | |
|---|---|---|
| 1,087,845 | 2/1914 | Stevens . |
| 1,213,001 | 1/1917 | Philips . |
| 1,248,492 | 12/1917 | Hill . |
| 1,527,291 | 2/1925 | Zorraguin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,535,773 | 8/1985 | Yoon . |
| 4,601,710 | 7/1986 | Moll . |
| 4,654,030 | 3/1987 | Moll et al. . |
| 4,828,547 | 5/1989 | Sahi et al. . |
| 4,869,717 | 9/1989 | Adair . |
| 4,902,280 | 2/1990 | Lander . |
| 4,931,042 | 6/1990 | Holmes et al. . |
| 4,943,280 | 7/1990 | Lander . |
| 5,030,206 | 7/1991 | Lander . |
| 5,053,016 | 10/1991 | Lander . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,152,754 | 10/1992 | Plyley et al. . |
| 5,158,552 | 10/1992 | Borgia et al. ........................... 604/165 |
| 5,207,647 | 5/1993 | Phelps . |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 1435246 | 11/1988 | U.S.S.R. . |
| 904635 | 8/1962 | United Kingdom . |
| 9210974 | 7/1992 | WIPO ................................... 128/753 |
| 9304632 | 3/1993 | WIPO . |
| 9304715 | 3/1993 | WIPO . |
| 9304716 | 3/1993 | WIPO . |
| 9317626 | 9/1993 | WIPO . |

*Primary Examiner*—Guy V. Tucker

[57] ABSTRACT

A safety needle instrument for penetrating a wall of an anatomical cavity to gain access to the anatomical cavity includes a needle having a sharp distal end for penetrating the anatomical cavity wall, a distally biased safety member having a distal end movable between an extended position protecting the sharp distal end of the needle and a retracted position exposing the sharp distal end of the needle, a handle for manually moving the safety member to the retracted position and a locking and releasing mechanism for locking the safety member in the retracted position and releasing the safety member to return to the extended position in response to distal movement of an operating member upon penetration of the safety needle instrument into the anatomical cavity, the operating member being preferably carried by the needle.

25 Claims, 9 Drawing Sheets

U.S. PATENT DOCUMENTS

| | | |
|---|---|---|
| 5,215,526 | 6/1993 | Deniega et al. . |
| 5,224,951 | 7/1993 | Freitas . |
| 5,224,952 | 7/1993 | Deniega et al. . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 11/1993 | Deniega . |
| 5,275,583 | 1/1994 | Crainich . |
| 5,290,304 | 3/1994 | Storace ................. 606/184 |
| 5,295,993 | 3/1994 | Green ................... 606/184 |
| 5,312,354 | 5/1994 | Allen et al. ............. 604/157 |
| 5,318,580 | 6/1994 | Gresl, Jr. ............... 606/185 |

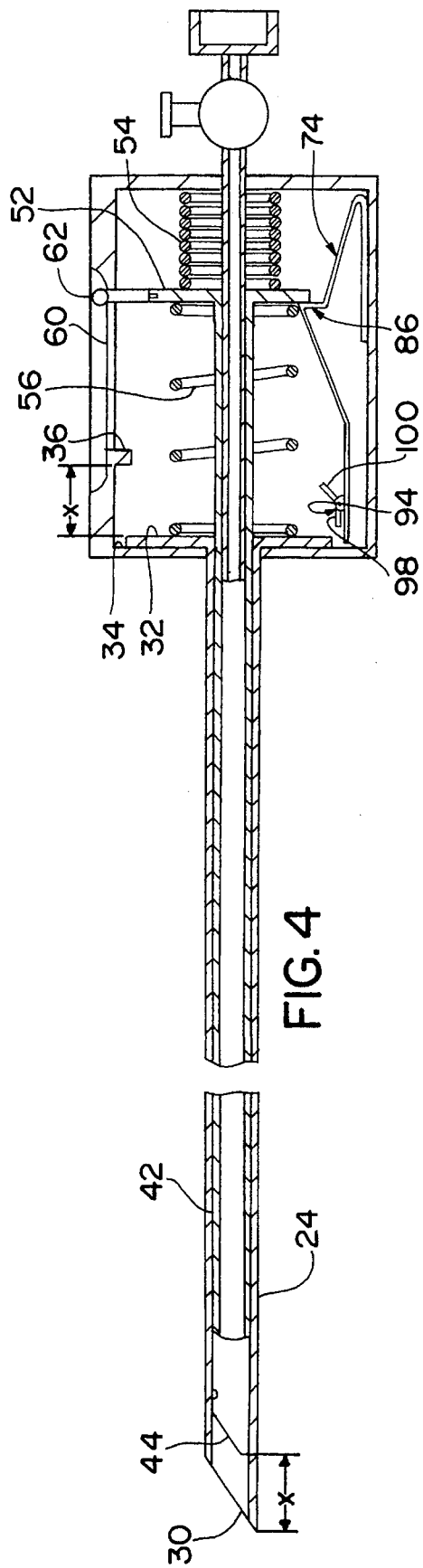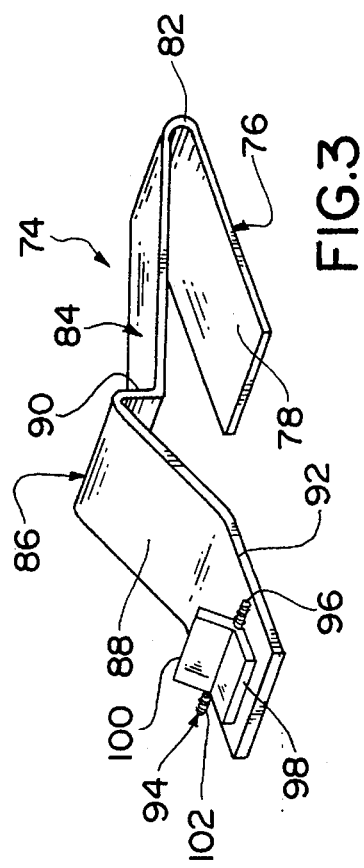

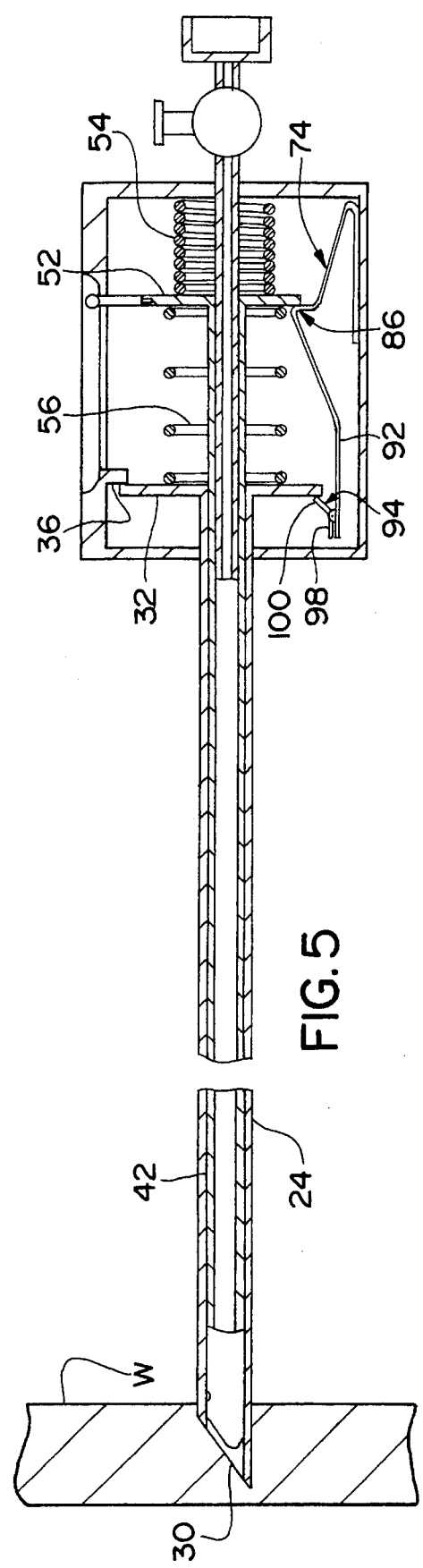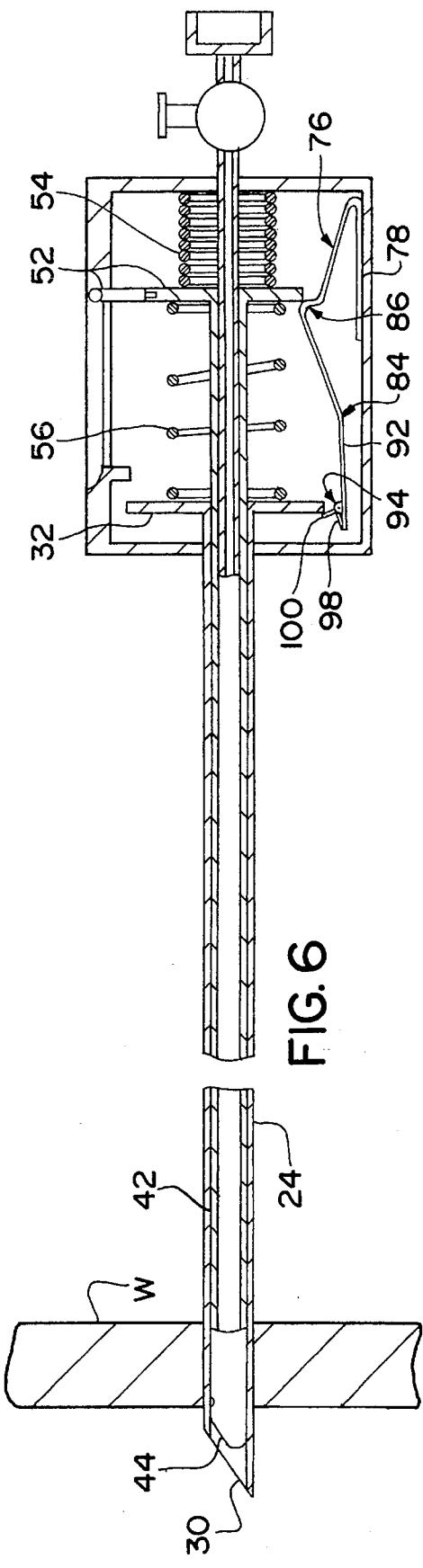

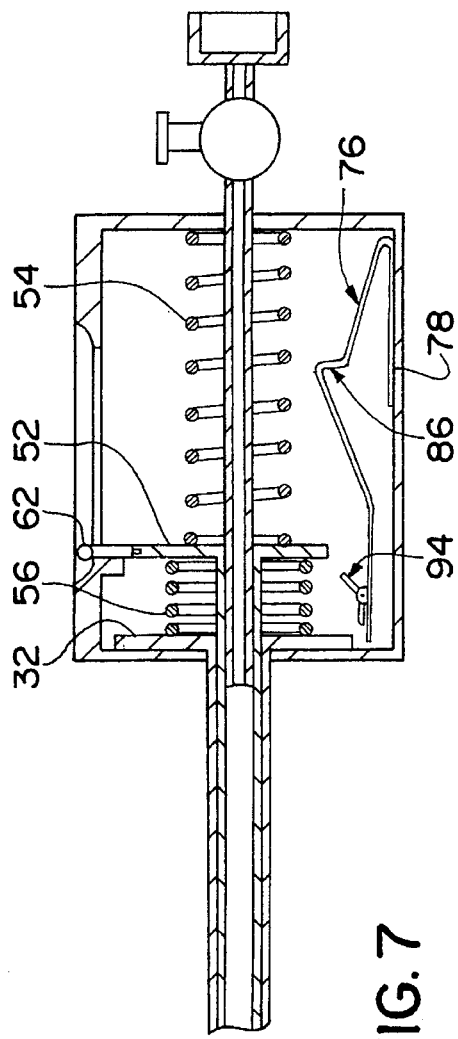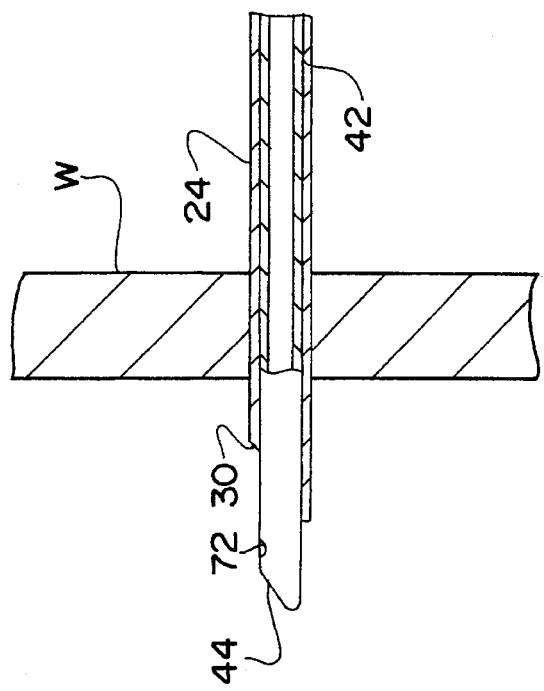
FIG. 7

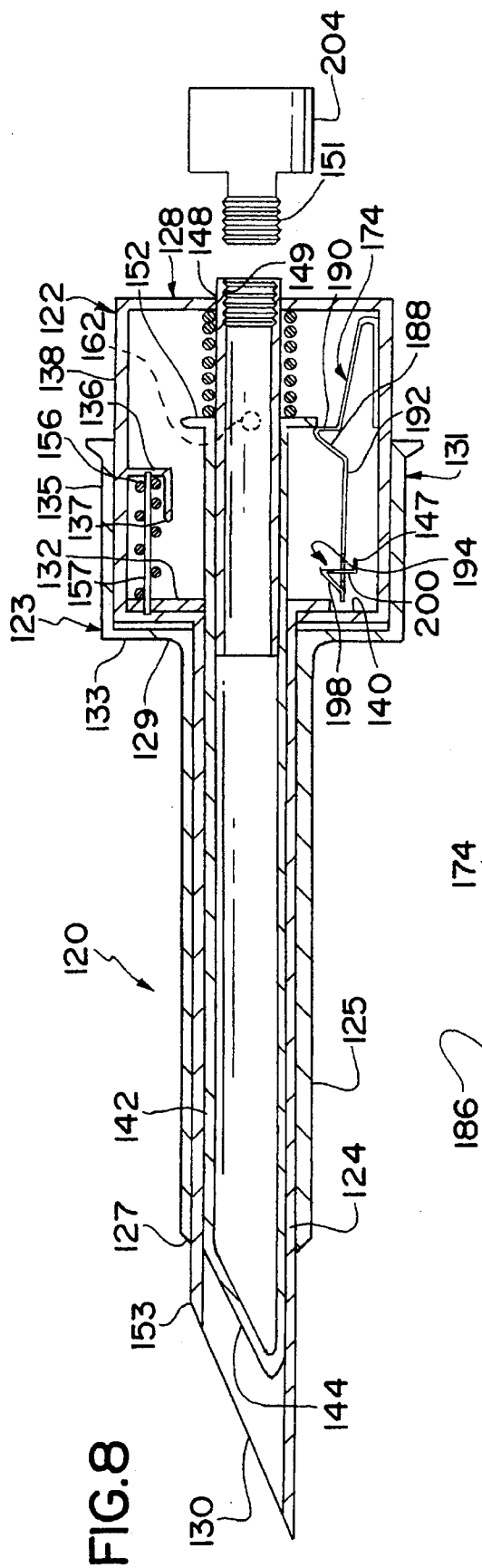
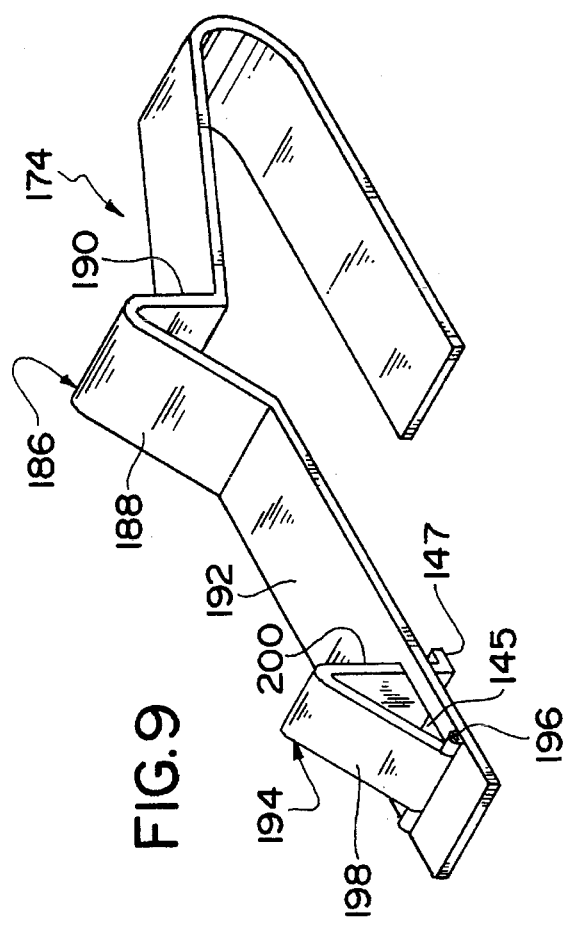
FIG.8
FIG.9

SAFETY NEEDLE INSTRUMENT HAVING A TRIGGERED SAFETY MEMBER

CROSS-REFERENCE TO RELATED APPLICATIONS

This application is a continuation-in-part of applications Ser. No. 08/083,220 filed Jun. 24, 1993, now U.S. Pat. No. 5,431,635, and Ser. No. 08/083,728 filed Jun. 29, 1993, now U.S. Pat. No. 5,466,224, the disclosures of which are incorporated herein by reference.

BACKGROUND OF THE INVENTION

1. Field of the Invention

The present invention pertains to safety needle instruments and, more particularly, to safety needle instruments including needles having sharp tips for penetrating anatomical tissue and safety members spring biased to an extended, protruding position to prevent inadvertent contact with tissue by the sharp needle tips.

2. Discussion of the Prior Art

Safety needle instruments have been proposed to gain access to anatomical cavities for many various procedures. Proposed safety needle instruments typically include a needle having a sharp tip for penetrating anatomical tissue and a safety member biased to move to an extended, protruding position to cover the sharp tip of the needle once the needle has entered the anatomical cavity. Accordingly, the safety member protects tissue and organ structures within the anatomical cavity from accidental injury by contact with the sharp tip of the needle after penetration or puncture of a wall of the anatomical cavity.

When the penetrating procedure is commenced, the distal end of the safety needle instrument is placed in contact with the anatomical cavity wall; and, as force is exerted on the safety needle instrument, contact of the safety member with the cavity wall moves the safety member proximally to a retracted position against the spring bias to expose the sharp tip of the needle to permit the sharp tip to penetrate the cavity wall. Accordingly, the force required to penetrate the cavity wall includes not only the force required to pass the safety needle instrument through the anatomical cavity wall but also the force required to overcome the spring bias on the safety member. Once the sharp tip of the needle has entered the anatomical cavity, the spring bias on the safety member overcomes the reduced proximal force on the safety member causing the safety member to move distally to the extended, protruding position. In practice, however, a residual proximal force is still applied to the safety member after penetration of the sharp needle tip into the cavity due to contact with surrounding tissue and/or tissue trapped between the safety member and the cannula and/or the needle, and the residual force is capable of preventing distal movement of the safety member to the extended, protruding position. To assure distal movement of the safety member upon entry of the safety needle instrument into the anatomical cavity, the strength of the spring biasing the safety member distally can be increased; however, increasing the strength of the bias spring also increases the force required to penetrate the cavity wall which is undesirable. Accordingly, currently available safety needle instruments with safety members utilize bias springs of strengths compromising force-to-penetrate and assured safety member distal movement in an attempt to satisfy both requirements.

SUMMARY OF THE INVENTION

Accordingly, it is a primary object of the present invention to improve safety needle instruments of the type having a needle and a safety member biased distally to protrude beyond a distal end of the needle by easing penetration and assuring protrusion of the safety member.

Another object of the present invention is to reduce the force-to-penetrate required to penetrate an anatomical cavity wall with a safety needle instrument of the type having a distally biased safety member with a blunt distal end for protruding beyond a sharp distal end of a needle once penetration into the cavity has been achieved.

A further object of the present invention is to increase the force biasing a safety member distally in a safety needle instrument to assure protrusion of the safety member after penetration into an anatomical cavity without increasing the force-to-penetrate required for penetration.

The present invention has an additional object in that a distally biased safety member is locked in a retracted position to expose a sharp distal end of a needle prior to contacting a wall of an anatomical cavity to be penetrated and is released to allow movement of the safety member to an extended position upon penetration into the anatomical cavity.

Another object of the present invention is to trigger release of a distally protruding safety member in response to distal movement of a needle upon penetration into an anatomical cavity.

A further object of the present invention is to utilize a strong spring to distally bias a safety member in a safety needle instrument to provide a shock absorber or cushion action without increasing the force-to-penetrate of the safety needle instrument.

Some of the advantages of the safety needle instrument of the present invention over the prior art are that the distal biasing force on a safety member can be designed to assure protrusion of the safety member upon penetration regardless of the anatomical cavity being penetrated, the force-to-penetrate of a safety needle instrument can be reduced to permit use in delicate tissue, the safety needle instrument can be used as a standard needle, a safety member protected needle or a triggered safety member protected needle without requiring a complex mechanism, and the safety needle instrument can be inexpensively manufactured with minimum components to reduce cost and allow economical single patient use.

These and other objects, benefits and advantages are realized with the present invention as generally characterized in a safety needle instrument including a needle having a sharp distal end for penetrating anatomical tissue, a safety member having a distal end and being movable relative to the needle between an extended, protruding position where the safety member distal end protrudes distally of or protects the sharp distal end of the needle and a retracted position where the safety member distal end is disposed proximally of the sharp needle distal end to expose the sharp needle distal end, bias means for biasing the safety member to move distally toward the extended position and for permitting the safety member to move proximally toward the retracted position, a handle coupled with the safety member for moving the safety member to the retracted position, locking means for engaging the safety member to lock the safety member in the retracted position and releasing means including an operating member responsive to entry of the safety needle instrument into the anatomical cavity for triggering release of the locking means to permit the bias means to move the safety member to the extended position.

The above and still further objects, features and advantages of the present invention will become apparent from the following description of the preferred embodiments when considered in conjunction with the accompanying drawings wherein like reference numerals in the various figures are utilized to designate like components.

BRIEF DESCRIPTION OF THE DRAWINGS

FIG. 3 is a perspective view of a locking and releasing mechanism for the safety needle instrument of FIG. 1.

FIG. 4 is a broken longitudinal section of the safety needle instrument of FIG. 1 with the safety member in a locked, retracted position.

FIG. 5 is a broken longitudinal section of the safety needle instrument of FIG. 1 with the needle moved proximally during penetration of an anatomical cavity wall.

FIG. 6 is a broken longitudinal section of the safety needle instrument of FIG. 1 with the needle moved distally to release the safety member.

FIG. 7 is a broken longitudinal section of the safety needle instrument of FIG. 1 with the safety member in the extended position after penetrating into an anatomical cavity.

FIG. 8 is a broken longitudinal section of another embodiment of a safety needle instrument according to the present invention with the safety member in the locked, retracted position.

FIG. 9 is a perspective view of a locking and releasing mechanism for the safety needle instrument of FIG. 8.

DESCRIPTION OF THE PREFERRED EMBODIMENTS

Figure 1:
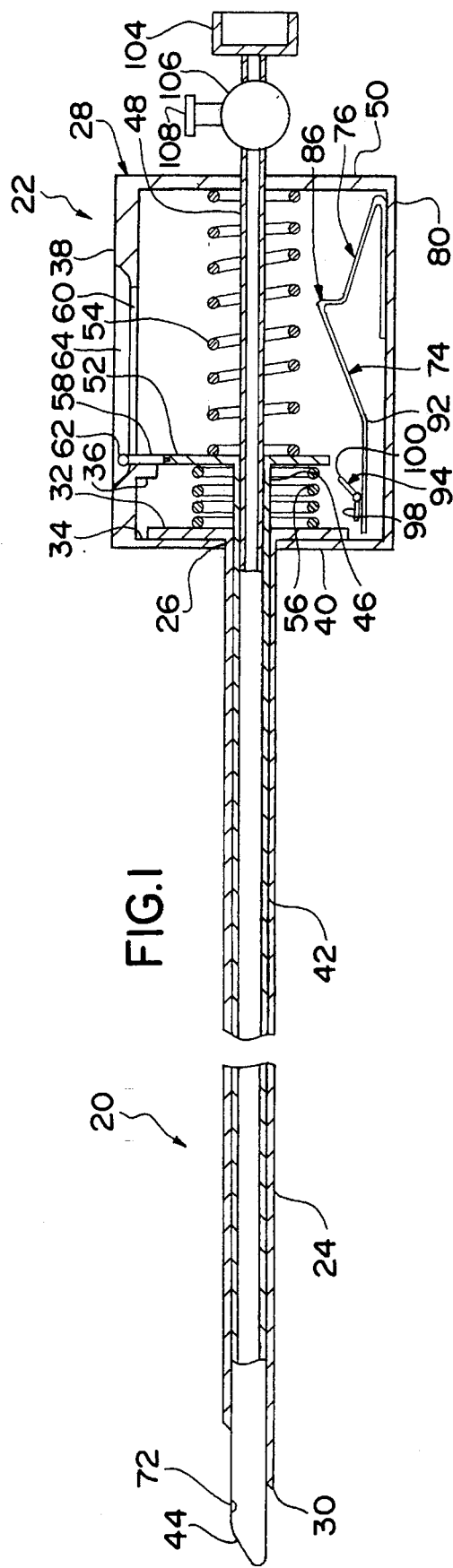
FIG. 1 is a broken longitudinal section of a safety needle instrument according to the present invention with the safety member in an extended, distally protruding position.
Figure 2:
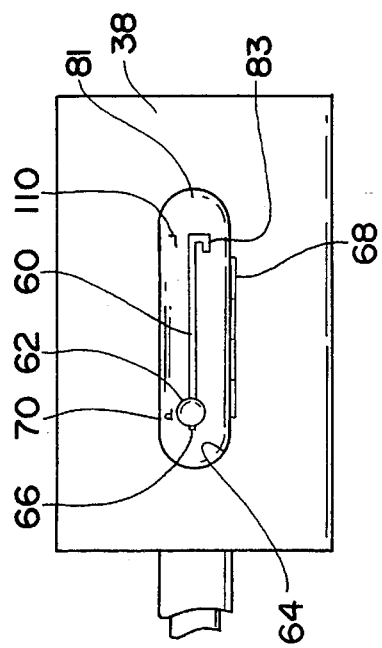
FIG. 2 is a top view of the hub of the safety needle instrument of FIG. 1.

A safety needle instrument 20 according to the present invention is shown in FIGS. 1 and 2 and is formed of a needle unit 22 including a cannulated, elongate, hollow, tubular needle 24 terminating at a proximal end 26 received in a hub 28 and at an angled, open, sharp distal end or tip 30 with a lumen extending between the proximal and distal ends. The needle unit 22 can be manufactured in a manner to be disposable for single patient use or to be sterilizable for reuse. The needle can be made of any suitable, medical grade materials, such as stainless steel. The distal end 30 can have any needle configuration desired by a surgeon for a particular procedure, for example, the curved configuration shown in FIG. 14 as will be explained further below. The proximal end 26 of needle 24 terminates at a transversely extending flange 32 positioned in hub 28 between spaced stops 34 and 36 depending from a top wall 38 of the hub, the stop 34 corresponding to a front wall 40 of the hub with the needle slidably passing through an opening in the front wall.

A safety member or probe 42 is slidably disposed in needle 24 and has an elongate, cylindrical configuration between a blunt distal end 44 and a proximal end 46 received in hub 28. The safety probe can be made of any suitable, medical grade materials, such as plastic, can be made of multiple components and can have any desired configuration in cross section, preferably corresponding to the cross sectional configuration of the needle. The blunt distal end 44 can have various configurations to protect tissue within an anatomical cavity by covering or protruding beyond the distal tip of the needle; however, it is preferred that the blunt distal end 44 have a configuration corresponding to the configuration of the open distal end 30 of the needle. As illustrated in FIG. 1, blunt distal end 44 is disposed at an angle to a longitudinal axis of the needle 24 substantially the same as the angle of needle distal end 30. The configuration of blunt distal end 44 is preferably smooth to protect tissue within an anatomical cavity from contact therewith and further to cover or protect the sharp distal tip 30 of the needle. Various configurations of safety members or probes useful with the present invention are disclosed in pending application Ser. No. 07/688,139 filed Dec. 26, 1990, the disclosure of which is incorporated herein by reference. The safety probe can be hollow in its entirety as shown in FIG. 1, partly hollow or at least the proximal end 46 thereof can be hollow or tubular with the proximal end 46 being open to receive a guide or control tube 48 extending through a rear wall 50 of the hub concentric with a longitudinal axis of the safety needle instrument. Proximal end 46 terminates at a transversely extending flange 52, and the distal and proximal ends of the safety probe can be connected in any suitable manner, such as a tubular shaft. The safety probe is mounted to slide over the guide tube against the bias of a helical spring 54 coiled around guide tube 48 and mounted in compression between flange 52 and hub rear wall 50. The needle 24 is biased distally by a helical spring 56 mounted in compression between flange 32 and flange 52 such that flange 32 is biased to abut stop 34, i.e., hub front wall 40 in FIG. 1, with the needle being slidable over the probe.

A pin 58 extends from flange 52 on the safety probe through a slot 60 in the top wall 38 of the hub to terminate at a handle or knob 62 positioned in an elongate, trough-like recess 64 in the top wall 38. As shown in FIG. 2, a transparent cover 81 is pivotally mounted on top wall 38 via a hinge 68 to cover recess 64 and allow handle 62 to slide thereunder. Slot 60 and recess 64 extend longitudinally in parallel with the longitudinal axis of the safety needle instrument, and the slot 60 has a distal end 66 and terminates proximally at a transversely extending J-shaped portion to define a locking proximal slot end 83. Spring 54 biases safety probe 42 distally toward an extended, protruding position where blunt distal end 44 protrudes beyond the sharp distal end 30 of needle 24 and handle 62 is adjacent the distal end 66 of slot 60 in alignment with indicia "P" 70 as shown in FIGS. 1 and 2. Where the safety probe is hollow as shown in FIG. 1, one or more than one hole or opening 72 communicating with the interior or lumen of the safety probe can be provided in the portion of the safety probe protruding beyond the needle distal end 30 for fluid communication with the anatomical cavity via control tube 48 as explained further below.

A locking and releasing mechanism 74 for locking the safety probe in a retracted position exposing the sharp distal end 30 of the needle and releasing the safety probe to allow the safety probe to return to the extended, protruding position is shown in FIGS. 1 and 3 and includes a latch or locking spring 76 made of a strip of resilient material formed to have a substantially flat base 78 secured to a bottom wall 80 of hub 28 and a bend 82 joining the base 78 with an upwardly angled arm 84 spaced from the base. Arm 84 carries a protruding latch 86 having a distal angled surface 88 joining a proximal latching surface 90 disposed substantially transversely to the longitudinal axis of the safety needle instrument and substantially parallel to the safety probe flange 52. Arm 84 has an extension 92 positioned distally of latch 86, and a releasing member or trigger 94 is juxtaposed with extension 92. The trigger 94 is pivotally mounted in the hub on a pin 96 secured to a wall or walls of the hub or a structure supported in the hub, and the trigger is generally L-shaped with a leg 98 overlying extension 92 and a leg 100 extending substantially transversely from leg 98 but at a slight angle toward the proximal end of the safety needle instrument. A torsion spring 102 is coiled around pin 96 and fixed to trigger 94 to bias the trigger counterclockwise, looking at FIGS. 1 and 3, such that leg 98 is biased toward extension 92.

Control or guide tube 48 extends proximally of hub 28 to terminate at a connector or fitting 104 disposed exteriorly of the hub for connection with a source or supply of fluid, such as insufflation gas, or suction. A valve, such as stop cock 106, can be disposed along guide tube 48 exteriorly of hub 28 to control fluid flow through the guide tube and, therefore, the safety needle instrument. Valve 106 can communicate with an additional connector or fitting 108 for connection with any system requiring fluid flow into or out of the body through the safety needle instrument.

In use, when a surgeon desires to penetrate into an anatomical cavity, such as a blood vessel or other organ or tissue structure, using the safety needle instrument 20, the instrument is in the condition shown in FIG. 1 with the safety probe 42 in the extended, protruding position to cover sharp distal tip 30 of the needle. Prior to commencing penetration of an anatomical wall W surrounding or defining the cavity, for example the wall of a vein or artery, cover 81 is pivoted out of the way with a finger, and handle 62 is grasped and manually moved proximally to move safety probe 42 proximally against the bias of spring 54 until flange 52 rides over latch 86 by engaging angled distal surface 88 to move arm 84 toward base 78. At this time, the surgeon can feel the flange 52 lock into place in engagement with latching surface 90 as arm 84 springs back and can also visually determine that the safety probe is in the locked, retracted position by noting the position of handle 62 in alignment with indicia "L" 110 disposed adjacent slot 60. The safety needle instrument 20 is now in the position illustrated in FIG. 4 with the safety probe 42 locked in the retracted position by locking and releasing mechanism 74 and the sharp distal end 30 of the needle 24 uncovered or exposed. The distance X between the needle distal end 30 and the safety probe distal end 44 is the same or substantially the same as the distance X between flange 32 on the proximal end of the needle and the stop 36. The needle is held in the extended position by the force from spring 56 which holds flange 32 against stop 34. In the position shown in FIG. 4, flange 32 is disposed distally of leg 100 of trigger 94.

When the sharp distal end 30 of the needle is brought into contact with the anatomical cavity wall W, the needle 24 moves proximally against the bias of spring 56 until flange 32 abuts stop 36 as shown in FIG. 5. The flange 32 forms an operating member cooperating with the locking and releasing mechanism 74; and, as the flange 32 moves proximally, the operating member formed thereby engages leg 100 to pivot trigger 94 clockwise, looking at FIG. 5, to allow the operating member to pass thereby. The clockwise pivotal movement of trigger 94 does not cause movement of the latch 86 since there is no engagement by either leg 98 or 100 with arm extension 92; and, once the operating member passes by leg 100, spring 102 returns trigger 94 to its normal position with leg 98 adjacent arm extension 92. Accordingly, as penetration of the anatomical cavity wall W is commenced, the force to penetrate is limited to the force required to cause sharp distal end 30 to pass through the cavity wall W since the safety probe is held in the retracted position by engagement of flange 52 with latch 86. That is, during penetration, no force is required to overcome the bias of spring 54. As penetration continues, the safety needle instrument will advance through the cavity wall W to the position shown in FIG. 6 wherein the needle 24 has passed entirely through the anatomical cavity wall W and begins to move distally under the force of spring 56. As the needle moves distally, the operating member formed by flange 32 engages leg 100 of trigger 94 causing the trigger to pivot counterclockwise, looking at FIG. 6, and causing leg 98 to engage extension 92 moving arm 84 toward base 78 against the force of spring strip 76. The movement of arm 84 away from the longitudinal axis of the safety needle instrument causes latch 86 to move out of engagement with flange 52 on the safety probe thereby allowing spring 54 to move the safety probe distally to the extended, protruding position where distal end 44 protrudes beyond the sharp distal tip 30 of the needle as illustrated in FIG. 7 thereby protecting tissue within the anatomical cavity from inadvertent contact with the sharp distal tip 38. When safety needle instrument 20 is used for introducing fluids into the cavity, such as an insufflation needle, subsequent to entry of the safety needle instrument into the anatomical cavity, the fluid, such as insufflation gas, is supplied to the interior of the safety probe to be introduced into the anatomical cavity via opening 72.

By forming spring 54 to be relatively strong, protrusion of the safety probe 42 is assured even should the safety probe engage tissue in the anatomical cavity wall or within the anatomical cavity or should any tissue be jammed between the safety probe and the needle. Additionally, the strong force of spring 54 provides the surgeon with the psychological benefit of knowing the safety probe is protecting the needle. Should tissue within the anatomical cavity be contacted by the distal end 44 of the safety probe, the safety probe can bounce or give a little in the manner of a shock absorber to protect such contacted tissue. Additionally, movement of the safety probe can be seen by the surgeon by noticing movement of handle 62 away from indicia 110 through the transparent cover 66. The strong force of spring 54 also provides the surgeon with an easily felt tactile signal that the safety probe has moved to the extended position and that penetration into the cavity has occurred which also can be visually confirmed by the position of handle 62 in alignment with indicia 70.

A locking mechanism can be provided in safety needle instrument 20 for locking the safety probe in the extended, protruding position. For example, the locking mechanism can include a locking finger normally in a position engaging flange 52 to prevent movement of the safety probe proximally and a control button for releasing the locking finger from engagement with the safety probe to permit proximal movement thereof as described in applicant's pending applications Ser. No 08/083,220 and Ser. No. 08/083,728. Accordingly, the locking mechanism can be utilized to permit automatic or selective locking of the safety probe in the extended, protruding position, if desired, by movement of the control button.

The latching operation produced by locking and releasing mechanism 74 can be disabled through the use of structure preventing latch 86 from engaging flange 52 on the proximal end of the safety probe. For example, an additional control button received in a groove or recess in arm 84 of locking and releasing mechanism 74 can be provided for moving arm 84 away from the longitudinal axis of the safety needle instrument to prevent latch 86 from engaging flange 52 as also described in applicant's pending patent applications Ser. No. 08/083,220 and Ser. No. 08/083,728. Accordingly, the safety needle instrument can operate like a standard safety needle.

By providing a locking mechanism for locking the safety probe in the extended position, the surgeon can selectively control the safety needle instrument to produce automatic locking of the safety probe upon penetration into the anatomical cavity. To allow the safety probe to be moved proximally either prior to penetration or after penetration, the surgeon utilizes the control button to move the locking finger out of the path of the flange 52. In a similar fashion, the additional control button on locking and releasing mechanism 74 allows the surgeon to selectively control operation of the locking and releasing mechanism 74 since the additional control button can be utilized to move latch 86 out of the path of safety probe flange 52. Accordingly, proximal movement of the safety probe cannot move flange 52 to a position where the flange engages latch 86; and, thus, the safety probe is free to move proximally and distally similar to a conventional safety needle. Thus, the safety needle instrument 20 can be used with the safety probe triggered by the operating member or with the safety probe free to move like a standard safety needle. Additionally, handle 62 can be moved to lock pin 58 in J-shaped proximal slot portion 68 such that the safety needle instrument 20 can be used as a standard needle since the safety probe is not free to move or to be triggered. Thus, with a single instrument, the surgeon has various options to be selected in accordance with particular procedures to be performed or particular surrounding circumstances.

Another embodiment of a safety needle instrument according to the present invention is shown at 120 in FIG. 8. Safety needle instrument 120 includes needle unit 122 and a catheter or cannula unit 123. The catheter unit 123 includes an elongate, cylindrical catheter or cannula 125 having a distal end 127 and a proximal end 129 secured to a housing 131. The catheter unit 123 can be made of any desirable, medical grade materials dependent upon procedural use and desirability of being for single patient use or reusable, and the catheter can be rigid, semi-rigid or flexible. Catheter distal end 127 can be beveled or angled, and the bevel or angle of the catheter distal end can be the same or substantially the same as the angle of the needle distal end 130. The housing 131 includes a forward wall 133 securing catheter proximal end 129 and a skirt 135 extending longitudinally from forward wall 133 in the proximal direction to terminate at an open rearward or proximal housing end. Housing 131 defines a recess for receiving hub 128 of needle unit 122 with the skirt 135 frictionally engaging hub 128. Needle unit 122 differs from needle unit 22 in that stop 136 is L-shaped, being made up of a partition depending from hub top wall 138 in the same direction as hub front wall 140 and a transverse ledge extending distally from the partition to terminate at an abutment or end 137 limiting proximal movement of needle 124. If desired, a guide rod 157 can be connected between hub front wall 140 and the stop 136 to extend through a slot in flange 132 with spring 156 coiled around the guide rod. Locking and releasing mechanism 174 for safety needle instrument 120 differs from locking and releasing mechanism 74 for safety needle instrument 20 in that trigger 194 for locking and releasing mechanism 174 includes distal and proximal legs 198 and 200, respectively, with distal leg 198 having an end pivotally mounted on a pin 196 on arm extension 192 and proximal leg 200 joined to an opposing end of leg 198 at a bend 143 as shown in FIG. 9. Leg 198 extends from arm extension 192 at an angle toward the proximal end of the safety needle instrument, and leg 200 is bent from leg 198 to extend substantially parallel to flange 132 of needle 124. Leg 200 extends through a slot 145 in arm extension 192 to terminate at a transverse, proximally extending projection 147 overlying arm extension 192. A torsion spring can be coiled around pin 196 and fixed to trigger 194 to bias the trigger 194 counterclockwise, looking at FIG. 9, such that projection 147 is biased toward arm extension 192. Guide tube 148 for safety needle instrument 120 differs from guide tube 48 for safety needle instrument 20 in that guide tube 148 has an internal thread 149 at a proximal end thereof for engaging an external thread 151 on a connector or fitting 204, and the fitting 204 can be provided without valve as shown in FIG. 8, or with a valve, such as stop cock 106, as shown in FIG. 1. Handle 162 for safety needle instrument 120 is arranged differently than handle 62 for safety needle instrument 20 in that handle 162 is mounted on a pin extending from safety probe flange 152 to be movable along a slot and recess provided in a side or lateral wall of hub 128 as shown by the position of handle 162 in dotted lines in FIG. 8.

The needle unit 122 and the catheter unit 123 can be provided to a surgeon separately or assembled together as shown in FIG. 8., and either or both of the catheter and needle units can be manufactured in a manner to be disposable for single patient use or to be sterilizable for reuse. The hub 128 can be coupled to the housing 131 by suitable detent or latch mechanisms if desired.

Use of the safety needle instrument 120 is similar to that described above with respect to safety needle instrument 20 in that, when a surgeon desires to penetrate into an anatomical cavity, the safety probe 142 will be in the extended, protruding position and will be moved proximally via handle 162 until flange 152 rides over angled distal surface 188 of latch 186 to be locked in the retracted position against proximal surface 190 as shown in FIG. 8. The sharp distal end 130 of the needle 124 tapers to a sharp tip or point from a junction 153 with the shaft of the needle, and the distance between Junction 153 and the distal end 127 of the catheter is substantially the same as the distance between the flange 132 on the proximal end of the needle and the stop 136. With the safety probe 142 in the retracted position, penetration of the cavity wall is commenced, and the force on the distal end of the needle will cause the needle to move proximally against the bias of spring 156. Additionally, flange 132 will move past trigger 194 causing the trigger to rotate in a clockwise direction so as not to cause movement of the latch. Upon entry into the anatomical cavity, the counter force on the distal end of the needle will be reduced allowing spring 156 to move the needle distally causing flange 132 to engage proximal leg 200 of trigger 194 and pivot the trigger counterclockwise causing projection 147 to engage arm extension 192. The engagement of projection 147 with extension 192 causes arm 184 to move toward base 178 moving the latch 186 out of engagement with flange 152 thereby allowing spring 154 to cause the safety probe to move distally to the extended, protruding position at which time the catheter distal end 127 will be within the anatomical cavity. With the distal end 127 of catheter 125 in the anatomical cavity, the needle unit 122 can be withdrawn from the catheter unit 123 leaving the catheter in place for connection with any desired system via the open end of housing 131 which can be a standard female Luer coupling.

Figure 10:
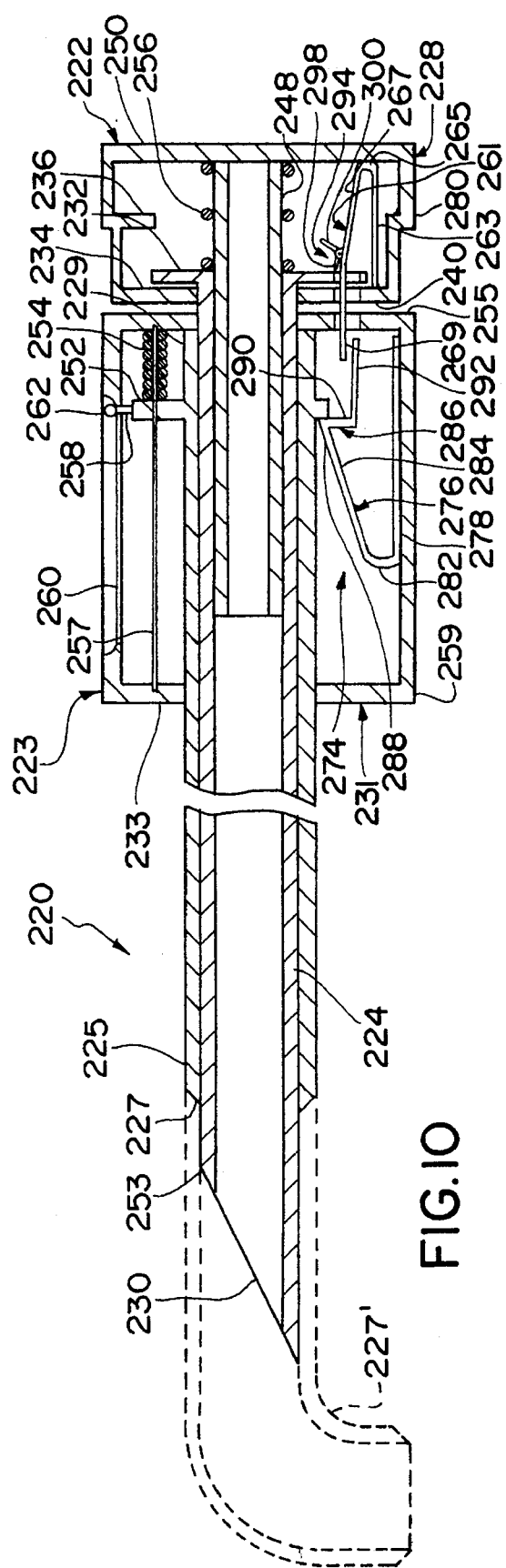
FIG. 10 is a broken longitudinal section of a further embodiment of a safety needle instrument according to the present invention with the safety member in the locked, retracted position.

An additional modification of a safety needle instrument according to the present invention is illustrated at 220 in FIG. 10, the safety needle instrument 220 differing from safety needle instrument 120 primarily in that the catheter 225 forms the safety member for safety needle instrument 220. Catheter unit 223 for safety needle instrument 220 includes catheter 225 terminating at a proximal end 229 disposed in housing 231 with the catheter extending slidably through an opening in front wall 233 of the housing. Housing 231 includes a rear wall 255 having an opening therein aligned with the opening in front wall 233 to allow passage therethrough by the needle 224. A transversely extending flange 252 is disposed on catheter 225 distally of proximal end 229 to be disposed in housing 231. The catheter 225 is biased distally by a helical spring 254 mounted in compression between flange 252 and housing rear wall 255. Spring 254 biases catheter 225 distally toward an extended, protruding position where blunt distal end 227 of the catheter protrudes beyond the sharp distal end 230 of the needle 224. If desired, a guide rod 257 can be connected between the front and rear housing walls to extend through a hole or opening in flange 252, and the spring 254 can be disposed around the guide rod.

Hub 228 has a forward end with a configuration in cross-section that is smaller than the cross-sectional configuration of housing 231 and a rearward end with a configuration in cross-section corresponding to the cross-sectional configuration of the housing to form a stepped configuration for hub 228 facilitating grasping of the housing and hub by a surgeon with one hand during use. Needle 224 terminates proximally at flange 232 positioned in hub 228 between stops 234 and 236 and is biased distally by a helical spring 256 coiled around guide tube 248 and mounted in compression between flange 232 and hub rear wall 250. A pin 258 extends from flange 252 on the catheter 225 through a slot 260 in housing 231 and terminates at a handle 262 with the handle being adjacent a distal end of the slot when the catheter is in the extended, protruding position as previously described for the safety member and hub of safety needle instrument 20.

Locking and releasing mechanism 274 for locking the catheter 225 in the retracted position exposing the sharp distal end 230 of the needle 224 and releasing the catheter to return to the extended position includes a latch or locking spring 276 made of a strip of resilient material formed to have a substantially flat base 278 secured to a bottom wall 259 of housing 231 and a bend 282 joining the base 278 with an upwardly angled arm 284 spaced from the base. Arm 284 carries a protruding latch 286 having a distal angled surface 288 joining a proximal latching surface 290 disposed substantially transversely to the longitudinal axis of the safety needle instrument and substantially parallel to the catheter flange 252. Arm 284 has an extension 292 positioned proximally of latch 286 and extending substantially parallel with a longitudinal axis of the safety needle instrument 220. The locking and releasing mechanism 274 also includes a releasing or trigger spring 261 made of a strip of resilient material formed to have a substantially flat base 263 secured to a bottom wall 280 of hub 228 and a bend 265 joining the base with an upwardly angled arm 267 spaced from the base. Arm 267 has an extension 269 positioned distally of a trigger 294, and the extension 269 passes through aligned openings in needle flange 232, hub front wall 240 and housing rear wall 255 to overlie extension 292 in housing 231. A trigger 294 includes a leg 298 overlying extension 269 and a leg 300 extending substantially transversely from leg 298 at a slight angle toward the proximal end of the safety needle instrument with the trigger being biased counterclockwise, looking at FIG. 10, such that leg 298 is biased toward extension 269.

In use of the safety needle instrument 220, the safety member will initially be in the extended, protruding position with the blunt distal end 227 of catheter 225 disposed beyond the sharp distal end 230 of the needle 224, and the needle will be biased distally by spring 256 such that flange 232 is adjacent the front wall of hub 228. In order to move the safety member to the retracted positioned shown in FIG. 10, the handle 262 is grasped to move the catheter 225 proximally until flange 252 rides over latch 286 by engaging angled distal surface 288 to move arm 284 toward base 278. Accordingly, catheter 225 will be in the retracted position shown in FIG. 10 with the junction 253 of the needle disposed beyond the distal end 227 of the catheter, and the distance that the junction is disposed beyond the distal end of the catheter is equal to the distance between flange 232 and stop 236. During penetration of a cavity wall, needle 224 will move proximally until flange 232 engages stop 236 in which position junction 253 will be aligned with the distal end 227 of the catheter. In this position, the operating member 232 will have moved passed the trigger 294 to be positioned just proximally of leg 300. Upon entry into the anatomical cavity, spring 256 will move needle 224 distally causing the operating member formed by flange 232 to engage leg 300 pivoting the trigger 294 to cause distal arm extension 269 to engage proximal arm extension 292 moving latch 286 out of engagement with flange 252 of the catheter and allowing spring 254 to move the catheter distally to the extended, protruding position overcoming tissue resistance of the wall. Once penetration is complete and the catheter is introduced into the cavity, the needle unit can be removed from the catheter unit leaving the catheter in place.

Figure 11:
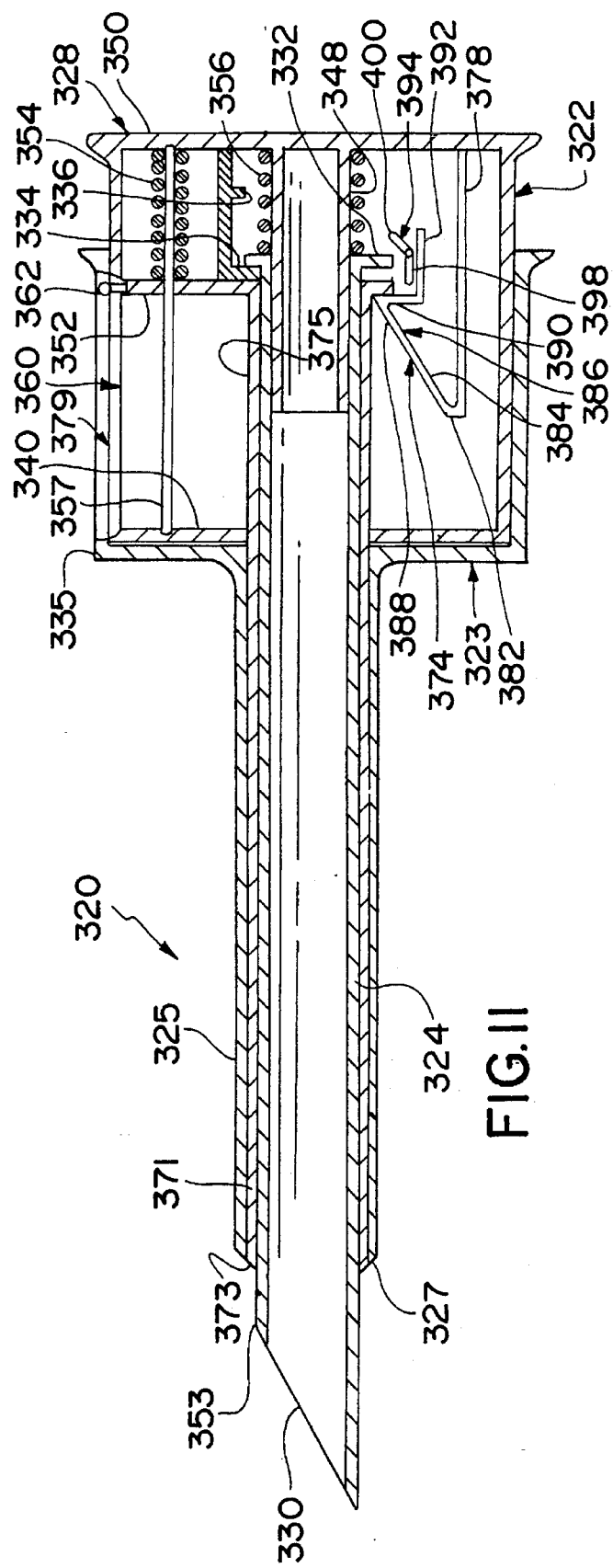
FIG. 11 is a broken longitudinal section of still another embodiment of a safety needle instrument according to the present invention with the safety member in the locked, retracted position.

A further embodiment of a safety needle instrument according to the present invention is shown at 320 in FIG. 11, the instrument 320 being particularly useful as an intravenous needle. The primary difference between safety needle instrument 320 and safety needle instruments 20, 120 and 220 is that a safety shield 371 is utilized in safety needle instrument 320 as the safety member. Safety needle instrument 320 includes catheter unit 323 similar to catheter unit 123 and a needle unit 322. Needle 324 of needle unit 322 terminates proximally at transversely extending flange 332 positioned in hub 328 between spaced stops or partitions 334 and 336 depending from a ledge extending distally from a rear wall of hub 328.

The safety shield 371 is slidably, concentrically disposed around needle 324 and has an elongate, cylindrical configuration between a blunt distal end 373 and a proximal end 375 received in hub 328. The safety shield can be made of any suitable, medical grade materials, such as plastic, can be made of multiple components and can have any desired configuration in cross-section. Preferably, the safety shield has a configuration corresponding to the cross-sectional configuration of the needle with an outer diameter or size to be received in catheter 325 and an inner diameter or size to receive the outer diameter or size of the needle. The blunt distal end 373 can have various configurations to protect tissue within an anatomical cavity by covering or protruding beyond the distal tip 330 of the needle; and, as shown in FIG. 11, distal end 373 is beveled or angled in a distal direction. The bevel or angle for the safety shield distal end is preferably the same or substantially the same as the angle of the sharp distal end 330 of the needle and the angle or bevel for the distal end 327 of the catheter. Proximal end 375 of the safety shield terminates at a transversely extending flange 352, and the distal and proximal ends of the safety shield can be connected in any suitable manner, such as by a tubular shaft.

The safety shield is mounted to slide over the needle against the bias of a helical spring 354 mounted in compression between flange 352 and hub rear wall 350. If desired, a guide rod 357 can be connected between hub front wall 340 and hub rear wall 350 with the guide rod passing through an opening in flange 352 and the spring 354 coiled around the guide rod. Needle 324 is biased distally by a helical spring 356 coiled around guide tube 348 and mounted in compression between flange 332 and the hub rear wall 350 such that flange 332 is biased to abut stop 334. A pin terminating at handle 362 extends from flange 352 on the safety shield through a slot 360 in the hub top wall aligned with a slot 379 in housing skirt 335. Spring 354 biases safety shield 371 distally toward an extended, protruding position where blunt distal end 373 protrudes beyond the sharp distal end 330 of needle 324 and handle 362 is adjacent the distal ends of slots 360 and 379.

Locking and releasing mechanism 374 for safety needle instrument 320 includes a latch or locking spring made of a strip of resilient material formed to have a substantially flat base 378 secured to a rear wall of hub 228 and a bend 382 joining the base with an upwardly angled arm 384 spaced from the base. Arm 384 carries or defines a protruding latch 386 having a distal angled surface 388 joining a proximal latching surface 390 disposed substantially transversely to the longitudinal axis of the safety needle instrument and substantially parallel to the safety shield flange 352. Arm 384 has an extension 392 positioned proximally of latch 386, and a releasing member or trigger 394 is juxtaposed with extension 392. Trigger 394 is generally L-shaped with a leg 398 overlying arm extension 392 and a leg 400 extending substantially transversely from leg 398 at a slight angle toward the proximal end of the safety needle instrument. Trigger 394 can be biased counterclockwise, looking at FIG. 11, such that leg 398 is biased toward extension 392.

In use, prior to penetration into an anatomical cavity, the safety member of the safety needle instrument 320 will be in the extended, protruding position with the distal end 373 of the safety shield 371 disposed beyond the distal end 330 of needle 324 to cover the sharp needle tip. Prior to commencing penetration of a wall of an anatomical cavity, handle 362 is grasped and manually moved proximally to move safety shield 371 proximally against the bias of spring 354 until flange 352 rides over latch 386 by engaging angled distal surface 388 to move arm 384 toward base 378. The safety shield is now locked in the retracted position by locking and releasing mechanism 374 with the distal end 373 of the safety shield aligned with the distal end 327 of the catheter and the sharp distal end 330 of the needle uncovered or exposed. The distance between the needle junction 353 and the distal ends of the catheter and the safety shield is substantially the same as the distance between the flange 332 and the stop 336. During penetration of the anatomical cavity wall, the needle 324 moves proximally against the bias of spring 356 until flange 332 abuts stop 336. As the flange 332 moves proximally, the operating member formed thereby engages leg 400 to pivot trigger 394 clockwise looking at FIG. 11 to allow the operating member to pass thereby. The clockwise pivotal movement of trigger 394 does not cause movement of the latch 386; and, once the operating member passes by leg 400, spring 376 returns trigger 394 to its normal position with leg 398 adjacent extension 392. Upon penetration into the anatomical cavity, needle 324 begins to move distally under the force of spring 356 causing the operating member formed by flange 332 to engage leg 400 causing the trigger 394 to pivot counterclockwise such that leg 398 engages extension 392 to move arm 384 toward base 378. The movement of arm 384 away from the longitudinal axis of the safety needle instrument causes latch 386 to move out of engagement with flange 352 on the safety shield thereby allowing spring 354 to move the safety shield distally to the extended, protruding position where distal end 373 protects or protrudes beyond the sharp distal tip 330 of the needle. Accordingly, when the needle unit 322 is removed from the catheter unit 323 after disengagement of the pin from the slot, the safety shield will cover the needle to protect against inadvertent contact with the needle by medical personnel.

Figure 12:
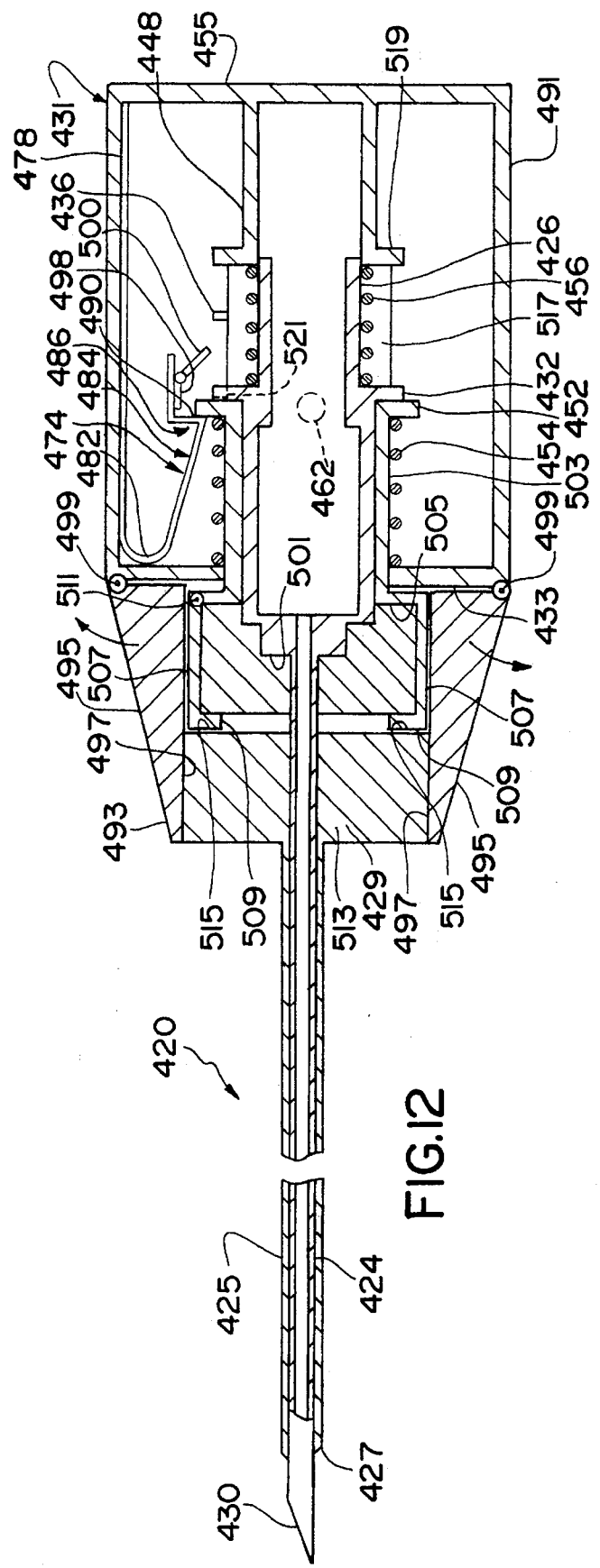
FIG. 12 is a broken longitudinal section of yet a further embodiment of a safety needle instrument according to the present invention with the safety member in the locked, retracted position.
Figure 13:
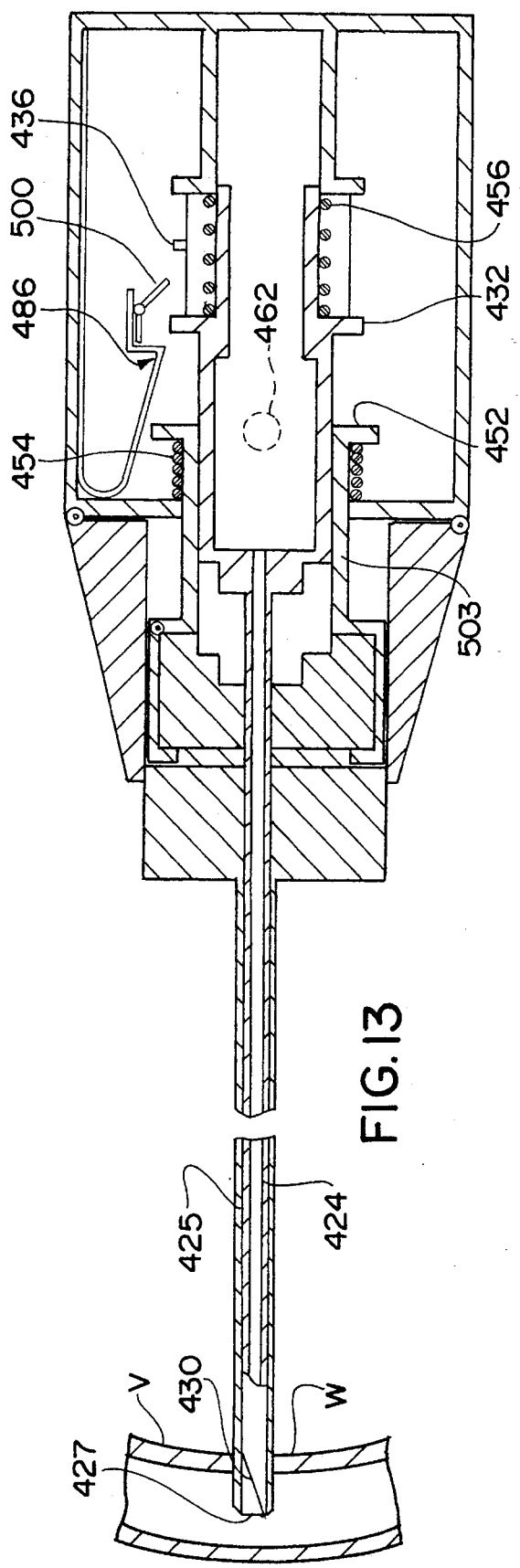
FIG. 13 is a broken longitudinal section of the safety needle instrument of FIG. 12 with the safety member in the extended position after penetrating into a vein.

A still further embodiment of a safety needle instrument according to the present invention is shown at 420 in FIGS. 12 and 13 and includes a combined catheter and needle unit made up of a housing 431 securing the needle proximal end 426 and the catheter proximal end 429. Housing 431 includes a housing body 491 that can be cylindrical, rectangular or any other desired configuration in cross-section facilitating grasping by a surgeon during use and a skirt 493 extending distally from a forward wall 433 of housing body 491. Skirt 493 can have a tapered configuration in the distal direction to facilitate grasping; and, as shown, the skirt 493 has a truncated conical configuration to facilitate a thumb grip. Skirt 493 defines an internal recess or passage and has an open distal end aligned with an opening in the housing body forward wall 433. Skirt 493 includes opposing clamp portions 495 that are pivotal or movable relative to the housing body 491 in a direction outwardly of a longitudinal axis of the safety needle instrument 420 from a lock position shown in FIG. 12 wherein inner clamping surfaces 497 of the clamp portions are engaged with catheter proximal end 429 to an unlock position wherein the clamping surfaces are disengaged from the catheter as shown by the arrows in FIG. 12. Skirt 493 can be split or slit longitudinally along less than the full length of the skirt to form clamp portions 495 with the clamp portions being joined to one another by a proximal peripheral section of the skirt, or the clamp portions can be made as separate pieces. Clamp portions 495 can be pivotally mounted to the housing body 491 along hinges or pivot pins 499, or the clamp portions can be made of a resilient, flexible or deformable material, such as spring material, to allow the clamp portions to be moved between the lock and unlock positions.

A guide tube 448 extends distally from a rear wall 455 of housing body 491 and has a transversely extending flange 519 and an enlarged forward section with a slot 517 therein extending distally of flange 519. The proximal end 426 of the needle is slidably disposed in the guide tube, and a catheter gripping member 503 is disposed around the needle. Catheter gripping member 503 has a transversely extending proximal flange 452 and a transversely extending distal flange 505 disposed in skirt 493 with the catheter gripping member passing through the opening in the housing body forward wall. Gripping arms 507 extend distally from flange 505 to terminate at transverse or perpendicular gripping fingers 509. At least one arm 507 is pivotally or movably mounted, such as by a hinge or pin 511, to distal flange 505 to permit pivotal movement of the arm in the direction outwardly of the instrument axis from a lock position shown in FIG. 12 wherein the arms extend substantially parallel to the instrument longitudinal axis to an unlock position wherein the arms are disposed outwardly. Movement of pivotal arm 507 outwardly of the instrument axis permits catheter 425 to be assembled with housing 431, and the proximal end 429 of the catheter has an enlarged cylindrical barrel 513 with external recesses 515 for locking of gripping fingers 509 therein when a proximal section of the barrel is inserted or pushed into the catheter gripping member. Pivotal arm 507 can be connected to the adjacent clamp portion 495 to move therewith to the unlock position in the direction outwardly of the instrument axis to release the catheter from fingers 509, and various mechanisms such as handles or knobs can be provided externally on housing 431 for pivoting the clamp portions 495 and/or the arms 507 together or individually. The clamp portions 495 and the arms 507 can be biased toward the longitudinal axis of the instrument to be normally disposed in the lock position and to be moved or pivoted to the unlock position by a force from catheter 425 being pushed into skirt 493 with the arms 507 snapping back into place to grip barrel 513. The clamp portions and arms can be biased in various ways such as with springs connected to hinges 497 and 511 and some other structure of the safety needle instrument, for example. By making the clamp portions and arms of spring material, the clamp portions and arms can be biased and made pivotal without the need for any separate hinge structure. The catheter gripping member 503 is biased distally by a spring 454 disposed around the catheter gripping member and mounted in tension between proximal flange 452 and housing body forward wall 433.

Needle proximal end 426 can be hollow or formed with an internal passage or channel and has an external configuration in cross-section to be slidably received in guide tube 448 and catheter gripping member 503 with the needle passing through the opening in the housing body forward wall. Needle 424 has a shoulder 501 disposed in skirt 493 and having a configuration corresponding to the configuration of the proximal end of the barrel 513. Needle 424 includes a transversely extending flange 432 positioned distally of a proximal most end of the needle and extending through slot 517. The needle is biased distally by a spring 456 disposed around the needle and mounted in compression between needle flange 432 and guide tube flange 519. A nub or projection 521 extends perpendicularly or transversely from needle flange 432 to ride along an outer surface or diameter of guide tube 448, and a raised stop or abutment 436 protrudes from the outer diameter or surface of the guide tube for engaging nub 521 to limit proximal movement of the needle. A handle 462 connected with flange 452 on the catheter gripping member is movable along a longitudinal slot provided in housing body 491.

The locking and releasing mechanism 474 for safety needle instrument 420 includes a latch or locking spring having a substantially flat base 478 secured to housing body 491 and a bend 482 joining the base 478 with a downwardly angled arm 484 spaced from the base. Arm 484 carries a protruding latch 486 having a distal angled surface 488 joining a proximal latching surface 490 disposed substantially transversely to the longitudinal axis of the safety needle instrument and substantially parallel to the intermediate flange 452. Arm 484 has an extension positioned proximally of latch 486, and a releasing member or trigger is juxtaposed with extension 492. Trigger 494 is generally L-shaped with a leg 498 overlying extension 492 and a leg 500 extending substantially transversely from leg 498 but a slight angle toward the proximal end of the safety needle instrument.

In use, the safety needle instrument 420 can be supplied with the needle 424 and catheter 425 assembled with housing 431 or the instrument can be supplied without the catheter assembled to the housing. Where the instrument 420 is supplied without the catheter assembled to the housing, a catheter 425 suitable for use in the procedure to be performed is passed over the needle, and the clamp portions 495 are manually pivoted or moved in a direction outwardly of the instrument longitudinal axis to the unlock position, and the arm 507 is similarly moved from the lock position to the unlock position allowing insertion of barrel 513 into the catheter gripping member 503. Once the catheter 425 is inserted in the catheter gripping member, the clamp portions 495 and arms 507 are returned, manually or automatically, to the lock position wherein fingers 509 are disposed within recesses 515 to lock the catheter in place. The instrument will be in the condition shown in FIG. 12 with the catheter 425 in the extended, protruding position to cover sharp distal tip 430 of the needle 424. Prior to commencing penetration of an anatomical cavity, such as vein V, handle 462 is manually moved proximally to move catheter 425 proximally against the bias of spring 454 until flange 452 rides over latch 486. The catheter 425 is now locked in the retracted position by locking and releasing mechanism 474 and the sharp distal end 430 of the needle 424 is uncovered or exposed with flange 432 being held against flange 452 by the force from spring 456. When the sharp distal end 430 of the needle is brought into contact with the wall W of the vein, the needle moves proximally against the bias of spring 456 until flange 432 abuts stop 436. Once the needle 424 has penetrated the wall W, the needle begins to move distally under the force of spring 456 such that the operating member formed by flange 432 engages leg 500 of trigger 494 causing the trigger to pivot clockwise, looking at FIG. 12, and causing leg 498 to engage extension 492 moving arm 484 toward base 478. The movement of arm 484 away from the longitudinal axis of the safety needle instrument causes latch 486 to move out of engagement with flange 452 on the catheter gripping member 503 allowing spring 454 to move the catheter distally to the extended, protruding position wherein distal end 427 protrudes beyond the sharp distal tip 430 of the needle. Movement of the catheter distally causes the catheter to be pushed through the vein wall V with spring 454 overcoming the frictional tissue resistance to be introduced into the vein thusly ensuring proper placement of the catheter. The catheter is then released from housing 431 leaving the catheter in place in the vein.

Figure 14:
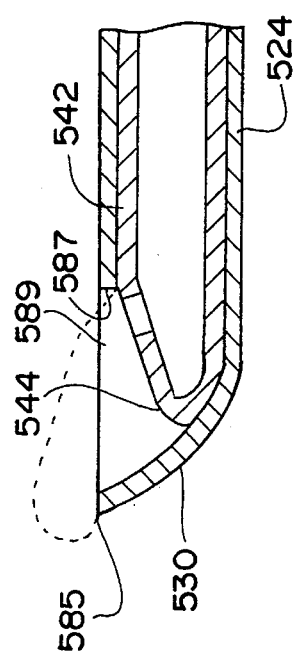
FIG. 14 is a broken longitudinal section of a modification of the needle and probe for use with the safety needle instrument according to the present invention.

A modification of a needle and safety probe useful in the safety needle instruments of the present invention is shown in FIG. 14 at 524 and 542, respectively. The primary difference between needle 524 and needle 24 is that needle 524 has a distal end 530 with a continuously curving configuration in a direction transverse to a longitudinal axis of needle 524 to terminate at a sharp distal tip or point 585 aligned with an edge 587 disposed along the outer diameter of the needle with an opening 589 extending between tip 585 and edge 587. The primary difference between safety probe 542 and safety probe 542 is that the distal end 544 of safety probe 542 is made of flexible, deformable, compressible or resilient material, such as rubber or sponge, to be disposed proximally of tip 585 in the retracted position and to have a non-linear bulging configuration extending from opening 589 to protect tip 585 in the extended position.

Release of the safety member to move proximally to the extended position can be triggered by movement of an operating member carried on any member movable in response to the needle entering the anatomical cavity. As described above, the operating member is carried by the needle to limit the number of components in the safety needle instrument; however, the operating member could be carried on an additional member or probe movable in response to penetration into the anatomical cavity. The safety member can have various configurations so long as the distal end protrudes beyond or protects the sharp tip of the penetrating member to provide a protective function, and a plurality of safety members can be employed in the safety needle instrument, for example by having a plurality of safety probes passing alongside or through the needle or by having a multi-component safety shield. Similarly, various bias means can be used in the safety needle instrument to produce movement of the operating member and the safety member including, for example, tension or compression coiled springs, rubber or plastic or magnets.

The components of the safety needle instruments of the present invention can be made of any suitable, medical grade materials to permit sterilization for reuse or for single patient use. With respect to the latter, the components can be made of multiple parts of various configurations and materials to reduce cost. The catheter unit can have various valves, stop cocks, and seals in the housing to control fluid flow therethrough and conventional couplings, such as Luer locks.

The locking and releasing mechanisms require only a latch for locking the safety member in the retracted position and a trigger for releasing the latch in response to distal movement of an operating member; and, thus, it will be appreciated that various mechanisms can be employed to produce the locking and releasing functions such as, for example, multiple movably or pivotally mounted cams or pawls. Various locking and releasing mechanisms that can be simply modified for use in the safety needle instrument of the present invention are disclosed in applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578, filed Apr. 15, 1993, Ser. No. 07/929,338, filed Aug. 14, 1992 and Ser. No. 07/845,177, filed Sep. 15, 1992, the disclosures of which are incorporated herein by reference. The above applications disclose automatically retracting safety penetrating instruments such that modification of the locking and releasing mechanisms requires configuring the latches to lock a member in a retracted position rather than an extended position. The above applications also disclose various bias arrangements useful with the safety needle instrument of the present invention.

The term "cavity" as used herein includes existing anatomical spaces, such as spaces created by abdominal walls, blood vessels and other organ walls, as well as potential anatomical spaces, such as spaces created by separating or pushing apart adjacent tissue walls or layers. With respect to potential anatomical spaces, the safety needle instrument of the present invention is particularly advantageous due to the strong distal movement of the safety member pushing the tissue walls or layers apart. To hold a catheter or cannula in place after introduction into an anatomical cavity, particularly a potential anatomical space, the catheter or cannula can have a normal non-linear distal end configuration, such as the curved or bent distal end 227' shown in dashed lines in FIG. 10. By making the catheter or cannula of a flexible material having shape memory, it will have a linear or straight configuration in the retracted position and will return to the non-linear, bent or curved configuration after protrusion such that the catheter or cannula will be held in the cavity when the needle is withdrawn therefrom.

From the above, it will be appreciated that the safety needle instrument of the present invention permits use of strong bias springs to assure movement of the safety member to the extended, protective position without increasing the force to penetrate. Further, after penetration of the safety needle instrument into the anatomical cavity, the safety member acts as a shock absorber upon inadvertent contact with tissue which contact can be felt by the surgeon and visually determined by movement of the handle. Additionally, the safety needle instrument can be used as a standard needle, a standard safety needle or a triggered safety needle without requiring complex mechanisms. The features of the various embodiments described above can be combined in any manner desired dependent upon the requirements and complexity of the safety needle instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety needle instrument for penetrating anatomical tissue to gain access to an anatomical cavity comprising a hub;

a needle mounted by said hub and having a sharp distal end for penetrating anatomical tissue;

a safety member having a blunt distal end and being movable relative to said hub between an extended position where said safety member distal end protrudes distally from said sharp needle distal end and a retracted position where said safety member distal end is disposed proximally of said sharp needle distal end to expose said sharp needle distal end;

bias means for biasing said safety member to move distally relative to said hub toward said extended position and for permitting said safety member to move proximally relative to said hub toward said retracted position;

a handle coupled with said safety member to manually move said safety member proximally relative to said hub from said extended position to said retracted position;

a locking mechanism engageable with said safety member to lock said safety member in said retracted position; and a releasing mechanism responsive to entry of said safety needle instrument into the anatomical cavity to trigger release of said locking mechanism to permit said bias means to move said safety member distally relative to said hub from said retracted position to said extended position.

2. A safety needle instrument as recited in claim 1 wherein said needle has a proximal end and said safety member has a proximal end and wherein said hub receives said needle proximal end and said safety member proximal end and wherein said handle extends from said hub, said bias means biases said safety member to move distally relative to said hub toward said extended position, said locking mechanism is disposed in said hub at a position to automatically lock said safety member in said retracted position when said safety member is manually moved to said retracted position by said handle and said releasing mechanism triggers release of said locking mechanism to permit said bias means to move said safety member distally relative to said hub from said retracted position to said extended position.

3. A safety needle instrument as recited in claim 2 wherein said hub includes a wall having a slot therein and said handle includes a pin extending through said slot to terminate at a knob externally of said hub to be visible.

4. A safety needle instrument as recited in claim 3 wherein said safety needle instrument has a longitudinal axis and said slot is disposed substantially parallel with said axis for movement of said handle substantially along said longitudinal axis of said safety needle instrument.

5. A safety needle instrument as recited in claim 4 wherein said hub includes a transparent cover disposed over said slot and said knob.

6. A safety needle instrument as recited in claim 1 wherein said safety member distal end extends around said sharp needle distal end.

7. A safety needle instrument as recited in claim 1 wherein said needle is hollow and further including means for supplying fluid through said needle.

8. A safety needle instrument as recited in claim 1 wherein said needle is hollow and further including means for applying suction through said needle.

9. A safety needle instrument as recited in claim 1 wherein said safety member includes an internal passage, a portion protruding beyond said sharp needle distal end in said extended position and a hole in said protruding portion in communication with said passage.

10. A safety needle instrument as recited in claim 1 and further including an elongate catheter disposed around said needle and having a distal end for positioning in the anatomical cavity and a proximal end for positioning externally of the anatomical cavity.

11. A safety needle instrument as recited in claim 10 wherein said safety member includes said catheter.

12. A safety needle instrument as recited in claim 10 and further comprising a housing receiving said catheter proximal end, said needle passing through said housing whereby said needle can be withdrawn from said catheter leaving said catheter distal end within the anatomical cavity.

13. A safety needle instrument for penetrating anatomical tissue to gain access to an anatomical cavity comprising a needle having a sharp distal end for penetrating anatomical tissue;

a safety member having a blunt distal end and being movable relative to said needle between an extended position where said safety member distal end protrudes distally from said sharp needle distal end and a retracted position where said safety member distal end is disposed proximally of said sharp needle distal end to expose said sharp needle distal end;

bias means for biasing said safety member to move distally toward said extended position and for permitting said safety member to move proximally toward said retracted position;

a handle coupled with said safety member to manually move said safety member proximally to said retracted position;

a locking mechanism engageable with said safety member to lock said safety member in said retracted position; and a releasing mechanism responsive to entry of said safety needle instrument into the anatomical cavity to trigger release of said locking mechanism to permit said bias means to move said safety member to said extended position;

wherein said sharp distal end of said needle defines an opening and said safety member distal end extends through said needle sharp distal end.

14. A safety needle instrument for penetrating anatomical tissue to gain access to an anatomical cavity comprising a needle having a sharp distal end for penetrating anatomical tissue;

a hub mounting said needle;

a safety member having a blunt distal end and being movable relative to said needle and hub between an extended position where said safety member distal end protrudes distally from said sharp needle distal end and a retracted position where said safety member distal end is disposed proximally of said sharp needle distal end to expose said sharp needle distal end;

bias means for biasing said safety member to move distally toward said extended position and for permitting said safety member to move proximally toward said retracted position;

a handle coupled with said safety member to manually move said safety member proximally to said retracted position;

a locking mechanism engageable with said safety member to lock said safety member in said retracted position;

a releasing mechanism responsive to entry of said safety needle instrument into the anatomical cavity to trigger release of said locking mechanism to permit said bias means to move said safety member to said extended position; and needle bias means for biasing said needle distally and for permitting proximal movement of said needle and hub with respect to said hub and wherein said releasing mechanism includes an operating member coupled with said needle for triggering release of said locking mechanism when said needle bias means moves said needle distally upon penetration into the anatomical cavity.

15. A safety needle instrument for penetrating anatomical tissue to gain access to an anatomical cavity comprising a needle having a sharp distal end for penetrating anatomical tissue and a proximal end;

a hub receiving said needle proximal end;

needle bias means for biasing said needle distally relative to said hub and permitting proximal movement of said needle relative to said hub in response to a force on said needle distal end;

a safety member having a blunt distal end and being movable relative to said hub between an extended position where said safety member distal end protrudes distally from said sharp needle distal end and a retracted position where said safety member distal end is disposed proximally of said sharp needle distal end to expose said sharp needle distal end;

safety member bias means for biasing said safety member to move distally relative to said hub toward said extended position and for permitting said safety member to move proximally relative to said hub toward said retracted position;

a locking mechanism engageable with said safety member to lock said safety member in said retracted position; and a releasing mechanism responsive to entry of said safety needle instrument into the anatomical cavity to trigger release of said locking mechanism to permit said safety member bias means to move said safety member distally relative to said hub from said retracted position to said extended position.

16. A safety needle instrument as recited in claim 15 wherein said safety member distal end extends around said sharp needle distal end.

17. A safety needle instrument as recited in claim 16 wherein said safety member includes a catheter disposed around said needle.

18. A safety needle instrument for penetrating anatomical tissue to gain access to an anatomical cavity comprising a needle having a sharp distal end for penetrating anatomical tissue and a proximal end;

a hub receiving said needle proximal end;

needle bias means for biasing said needle distally relative to said hub and permitting proximal movement of said needle relative to said hub in response to a force on said needle distal end;

a safety member having a blunt distal end and being movable relative to said needle between an extended position where said safety member distal end protrudes distally from said sharp needle distal end and a retracted position where said safety member distal end is disposed proximally of said sharp needle distal end to expose said sharp needle distal end;

safety member bias means for biasing said safety member to move distally toward said extended position and for permitting said safety member to move proximally toward said retracted position;

a locking mechanism engageable with said safety member to lock said safety member in said retracted position; and a releasing mechanism responsive to entry of said safety needle instrument into the anatomical cavity to trigger release of said locking mechanism to permit said safety member bias means to move said safety member to said extended position, wherein said releasing mechanism includes an operating member carried by said needle for triggering release of said locking mechanism upon said needle bias means moving said needle distally when said needle enters the anatomical cavity.

19. A safety needle instrument for penetrating anatomical tissue to gain access to an anatomical cavity comprising a needle having a sharp distal end for penetrating anatomical tissue and a proximal end;

a hub receiving said needle proximal end;

needle bias means for biasing said needle distally relative to said hub and permitting proximal movement of said needle relative to said hub in response to a force on said needle distal end;

a safety member having a blunt distal end and being movable relative to said needle between an extended position where said safety member distal end protrudes distally from said sharp needle distal end and a retracted position where said safety member distal end is disposed proximally of said sharp needle distal end to expose said sharp needle distal end;

safety member bias means for biasing said safety member to move distally toward said extended position and for permitting said safety member to move proximally toward said retracted position;

a locking mechanism engageable with said safety member to lock said safety member in said retracted position; and a releasing mechanism responsive to entry of said safety needle instrument into the anatomical cavity to trigger release of said locking mechanism to permit said safety member bias means to move said safety member to said extended position;

wherein said sharp end of said needle defines an opening and said safety member distal end extends through said sharp needle distal end.

20. A safety needle instrument for penetrating a wall of an anatomical cavity to gain access to the anatomical cavity comprising a housing;

an elongate, tubular catheter having a distal end for positioning in the anatomical cavity and a proximal end for positioning externally of the anatomical cavity wall;

a needle disposed in said catheter having a sharp distal end for penetrating the anatomical cavity wall;

a safety member mounted by said housing and having a blunt distal end, said safety member being movable relative to said housing between an extended position where said safety member distal end protrudes distally from said sharp needle distal end and a retracted position where said safety member distal end is disposed proximally of said sharp needle distal end to expose said sharp needle distal end;

bias means for biasing said safety member to move distally relative to said housing toward said extended position and for permitting said safety member to move proximally relative to said housing toward said retracted position;

a locking mechanism engageable with said safety member to lock said safety member in said retracted position; and a releasing mechanism including an operating member movable distally responsive to entry of said safety needle instrument into the anatomical cavity to trigger release of said locking mechanism to permit said bias means to move said safety member distally relative to said housing from said retracted position to said extended position.

21. A safety needle instrument for penetrating anatomical tissue to gain access to an anatomical cavity comprising a housing;

a needle having a sharp distal end for penetrating anatomical tissue and a proximal end mounted by said housing;

a catheter having a blunt distal end and a proximal end mounted by said housing, said catheter being movable relative to said housing between an extended position where said catheter distal end protrudes distally from said sharp needle distal end and a retracted position where said catheter distal end is disposed proximally of said sharp needle distal end to expose said sharp needle distal end;

bias means for biasing said catheter to move distally relative to said housing toward said extended position and for permitting said catheter to move proximally relative to said housing toward said retracted position;

a locking mechanism engageable with said catheter to lock said catheter in said retracted position prior to penetrating anatomical tissue; and a releasing mechanism responsive to entry of said safety needle instrument into the anatomical cavity to trigger release of said locking mechanism to permit said bias means to move said catheter distally relative to said housing from said retracted position to said extended position;

wherein said housing includes a gripping member releasably securing said catheter proximal end to said housing.

22. A safety needle instrument as recited in claim 21 wherein said gripping member includes gripping arms mounted in said housing and movable between a lock position engaging said catheter proximal end and an unlock position releasing said catheter proximal end from said housing.

23. A safety needle instrument as recited in claim 22 wherein said safety needle instrument includes a longitudinal axis and said gripping arms are pivotally mounted in said housing for movement toward said unlock position in a direction away from said longitudinal axis and toward said lock position in the direction of said axis.

24. A safety needle instrument as recited in claim 22 wherein said catheter proximal end includes an annular recess and said gripping arms include transverse fingers for engaging said recess in said lock position.

25. A safety needle instrument as recited in claim 22 wherein said housing includes a body and a portion extending distally from said body and said distally extending portion is pivotally mounted to said body for movement in the same direction as said gripping arms.

* * * * *